(12) United States Patent
Norris et al.

(10) Patent No.: US 12,262,696 B2
(45) Date of Patent: Apr. 1, 2025

(54) GAS MONITORING DEVICE

(71) Applicant: ZELP LTD, London (GB)

(72) Inventors: Francisco Norris, London (GB); Patricio Norris, London (GB)

(73) Assignee: ZELP LTD, London (GB)

( * ) Notice: Subject to any disclaimer, the term of this patent is extended or adjusted under 35 U.S.C. 154(b) by 1 day.

(21) Appl. No.: 17/787,077

(22) PCT Filed: Dec. 3, 2020

(86) PCT No.: PCT/GB2020/053103
§ 371 (c)(1),
(2) Date: Jun. 17, 2022

(87) PCT Pub. No.: WO2021/123726
PCT Pub. Date: Jun. 24, 2021

(65) Prior Publication Data
US 2023/0038208 A1 Feb. 9, 2023

(30) Foreign Application Priority Data

Dec. 20, 2019 (GB) ...................................... 1919071
Nov. 25, 2020 (GB) ...................................... 2018568

(51) Int. Cl.
*A01K 29/00* (2006.01)
*A01K 11/00* (2006.01)
(Continued)

(52) U.S. Cl.
CPC .......... *A01K 29/005* (2013.01); *A01K 11/006* (2013.01); *A61B 5/082* (2013.01);
(Continued)

(58) Field of Classification Search
CPC .... A01K 29/005; A01K 11/006; A61B 5/082; A61B 5/097; A61B 2503/40; A61B 2560/0214
See application file for complete search history.

(56) References Cited

U.S. PATENT DOCUMENTS 5,265,618 A * 11/1993 Zimmerman ........ G01N 33/497
600/531
2008/0078382 A1* 4/2008 LeMahieu ......... A61M 16/0069
128/200.24
(Continued)

FOREIGN PATENT DOCUMENTS

CN 204909457 U 12/2015
EP 3315965 A1 * 5/2018 ........... A01K 29/005
(Continued)

OTHER PUBLICATIONS

English-language machine translation of EP-3315965-A1 (Year: 2023).*

(Continued)

*Primary Examiner* — Andrey Shostak
(74) *Attorney, Agent, or Firm* — Foley & Lardner LLP (57) ABSTRACT

An animal emission monitoring device for positioning on cattle, the animal emission monitoring device comprising a snout member comprising a sensor unit for detecting the quantity of methane emissions and a positioning means for positioning the device on the head of an animal such that the snout member locates the sensor unit over the nostril of the animal.

24 Claims, 4 Drawing Sheets

(51) Int. Cl.
A61B 5/08 (2006.01)
A61B 5/097 (2006.01)

(52) U.S. Cl.
CPC .......... *A61B 5/097* (2013.01); *A61B 2503/40* (2013.01); *A61B 2560/0214* (2013.01)

(56) References Cited

U.S. PATENT DOCUMENTS

| | | | |
|---|---|---|---|
| 2008/0241886 | A1* | 10/2008 | Herrema .................. C12N 1/30 |
| | | | 435/189 |
| 2010/0279180 | A1 | 11/2010 | Herrema et al. |
| 2011/0192213 | A1* | 8/2011 | Zimmerman ............ A01K 5/02 |
| | | | 73/23.3 |
| 2012/0115240 | A1 | 5/2012 | Caldeira et al. |
| 2018/0146645 | A1* | 5/2018 | Arbel ................... A01K 11/006 |
| 2019/0175064 | A1* | 6/2019 | Haveri .............. A61M 16/0666 |
| 2020/0030629 | A1* | 1/2020 | Murphy ................ A61N 5/0618 |
| 2021/0161428 | A1* | 6/2021 | Demas ................. A61B 5/0836 |

FOREIGN PATENT DOCUMENTS

| | | |
|---|---|---|
| EP | 3 417 936 A1 | 12/2018 |
| GB | 2 577 227 A | 7/2021 |
| KR | 1020110047462 A | 1/2012 |
| KR | 20170036933 A | 4/2017 |
| RU | 2560985 C2 | 8/2015 |
| SU | 1318219 A1 | 6/1987 |
| WO | WO-01/47417 A1 | 7/2001 |
| WO | WO-2019/132803 A2 | 7/2019 |
| WO | WO-2021/030793 A | 2/2021 |

OTHER PUBLICATIONS

International Search Report and Written Opinion on PCT Appl. Ser. No. PCT/GB2020/053103 dated Feb. 23, 2021 (12 pages).
"Measurement of Methane Production from Ruminants"(Bhatta Raghavendra et al.) Asian-Australasian Journal of Animal Science 2007; 20(8): 1305-1318. https://doi.org/10.5713/ajas.2007. 1305 dated Jun. 27, 2007.
Foreign Search Report on non-Foley case related to US dated Jun. 19, 2020.
https://www.zelp.co/technology/—see whole p. 23 at least Archived on Oct. 5, 2020 and available from https://web. archive.org/web/20200510080606/https://www.zelp.co/technology/.
International Preliminary Report on Patentability for PCT/GB2020/053103 dated Jun. 30, 2022.
Office Action on GB Application No. GB2018568.2 dated May 25, 2021.
Russian Office Action on RU 2022116554/10(034947) dated Apr. 24, 2024.

* cited by examiner

GAS MONITORING DEVICE

CROSS-REFERENCE TO RELATED APPLICATIONS

This application is a U.S. National Stage Application under 35 U.S.C. § 371 of International Patent Application No. PCT/GB2020/053103, filed on Dec. 3, 2020, which claims priority to Great Britain Patent Application Nos. 2018568.2, filed on Nov. 25, 2020, and 1919071.9, filed on Dec. 20, 2019, the content of each of which is incorporated herein by reference in their entireties.

FIELD OF THE INVENTION

The present invention relates to an animal emission monitoring device for positioning on cattle.

BACKGROUND TO THE INVENTION

Methane is known to be a potent greenhouse gas, having a global warming potential that is considerably higher than that of carbon dioxide. Livestock are known to be a significant source of methane gas, which is released via exhalations and burping. With enormous variation of emission quantities between animals, it is important to measure and monitor the emissions of individual animals.

The methane emission of livestock often has direct economic consequences for livestock producers, who may be subject to taxes based on their carbon footprint. Additionally, with cattle being key contributors to global warming, it is vital to measure and monitor methane emissions from livestock to understand emission behaviour and create emission inventories. Measurement of methane gas emissions from livestock is also important for pharmaceutical companies and developers of nutrition for livestock, as it provides an indication of animal digestive efficiency.

Known methane measurement devices are bulky, high cost, require user operation and/or are not suitable for long-term use. For example, sensor-rigged rooms known as respiratory chambers are expensive to operate and require containment of the animal for a number of weeks. Further, sensing devices employed in feeding troughs only measure methane emissions during feed times, and as such provide a limited insight into daily emissions. Additionally, user-held laser detection devices are only appropriate for very short-run monitoring of emissions.

Furthermore, optical gas imaging has shown that as close to 95% of methane emissions emitted from cattle comes from the nose and mouth, with the majority of these emissions exiting through the nostrils of the livestock. Known methane measurement devices fail to monitor cattle methane production directly from this greatest point of emission.

Objects and aspects of the present invention seek to alleviate at least these problems with the prior art.

SUMMARY OF THE INVENTION

According to a first aspect of the invention, there is provided an animal emission monitoring device for positioning on cattle, the animal emission monitoring device comprising a snout member. The snout member comprises a sensor unit for detecting the quantity of methane emissions. The device further comprises positioning means for positioning the device on the head of an animal such that the snout member locates the sensor unit over the nostril of the animal.

In this way, continuous monitoring of emissions from animals is achieved over long periods of time. Further, emission data is taken from the greatest source of emissions of the animals, improving the accuracy of the data.

Preferably, the device comprises positioning means for positioning the device on the head of an animal such that the snout member is configured to extend from the upper side of the head of the animal such that the portion of the snout member in which the sensor unit is located projects over the nostril of the animal Preferably, the sensor unit comprises two sensors, each of said two sensors proximate each nostril of the animal.

Preferably, the sensor unit of the snout member is 1-5 cm from the nostril of the animal, in use. More preferably, the sensor unit of the snout member is 1-3 cm from the nostril of the animal, in use. Most preferably, the sensor unit of the snout member is 1-2 cm from the nostril of the animal, in use.

Preferably, the sensor unit collects data continuously. Alternatively, the sensor unit monitors intermittently. In this way, data is collected at irregular intervals. Alternatively, the sensor unit monitors at discrete intervals. Preferably, data is collected every 50-200 ms. More preferably, data is collected every 20-100 ms.

Preferably, the device further comprises a storing means for storing data collected from said sensor unit.

Preferably, data from said sensor unit is transmitted wirelessly to a gateway or user device. More preferably, the data from said sensor unit is transmitted in real time.

Preferably, the device further comprises a power means. More preferably, the power means comprises a battery. Further preferably, the power means comprises a solar cell. Further preferably, the battery is recharged by said solar cell.

Preferably, the solar cell requires no more than 5 hours of sunlight to fully recharge the power means. More preferably, the solar cell requires no more than 2 hours of sunlight to fully recharge the power means.

Preferably, the power means operates for at least 10 days before recharging is required. More preferably, the power means operates for at least 15 days before recharging is required.

Preferably, the sensor unit comprises at least one carbon dioxide sensor. More preferably, the sensor unit comprises two carbon dioxide sensors. Most preferably, the sensor unit comprises two carbon dioxide sensors, one sensor proximate each nostril of the animal.

Preferably, the device is waterproof.

Preferably, the snout member is substantially Y-shaped.

Preferably, the sensor unit comprises at least one pressure sensor. Preferably, the pressure sensor is a differential pressure sensor. Alternatively or additionally, the sensor unit comprises at least one flow rate sensor for measuring fluid flow rate.

Preferably, the device comprises a flexible member located, in use, over the nostril of the animal. Preferably, the flexible member is substantially curved. In this way, there is a reduction in the interference of wind, contaminants, and pre-dispersion of the exhalation and the methane capturing of the device is improved. The flexible member protects the sensors of the device against the elements and reduces dilution or pre-dispersion of the animal's exhalation prior to sensor capture.

Preferably, the flexible member is detachable. In this way, a flexible member of appropriate size for the dimensions of the animal's head and snout can be selected for use. As such, a flexible member which substantially shields the nostrils without an uncomfortable fit is provided. Alternatively, the flexible member is fixed to the emission monitoring device.

Preferably, the device comprises at least one temperature sensor. Alternatively or additionally, the device comprises at least one inertia sensor. Alternatively or additionally, the device comprises at least one location tracker. In this way, additional data regarding the context of the gas emission data can be monitored.

Data from the at least one temperature sensor and/or the at least one inertial sensor and/or the location tracker can signal the conditions on the animal during gas emission monitoring. Such data can assist with the analysis and monitoring of methane readings from the methane sensors. For example, by using an inertial measurement unit (IMU) or other inertial sensor, periods of feed activity can be detected and monitored. Typically, methane production and animal feed intake are correlated, namely methane production increases during feed intake. As such, if feed activity is decreasing, and methane activity is increasing, this signals that bacteria or parasites may be present in the animals' stomach.

Preferably, the snout member is adjustable. More preferably, the snout member is adjustable between a plurality of discrete positions.

Preferably, the device comprises at least one filter. In this way, feed, mud, grass and other contaminants are prevented from interfering with sensor function.

DETAILED DESCRIPTION

Embodiments of the present invention will now be described by way of example only and with reference to the accompanying drawings, in which.

Figure 1:
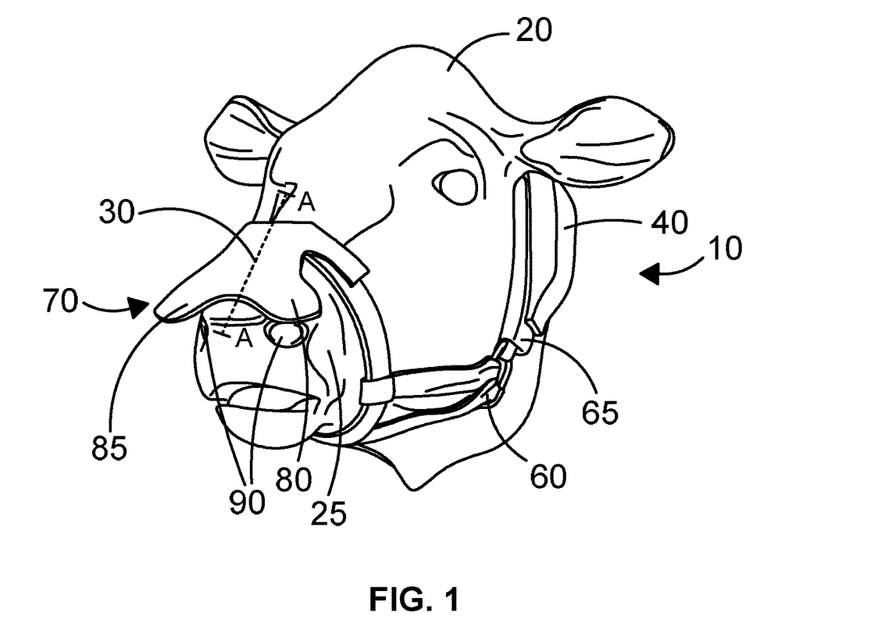
FIG. 1 depicts a perspective view of the animal emission monitoring device in accordance with the present claimed invention positioned on the head of a cow, in use.
Figure 2:
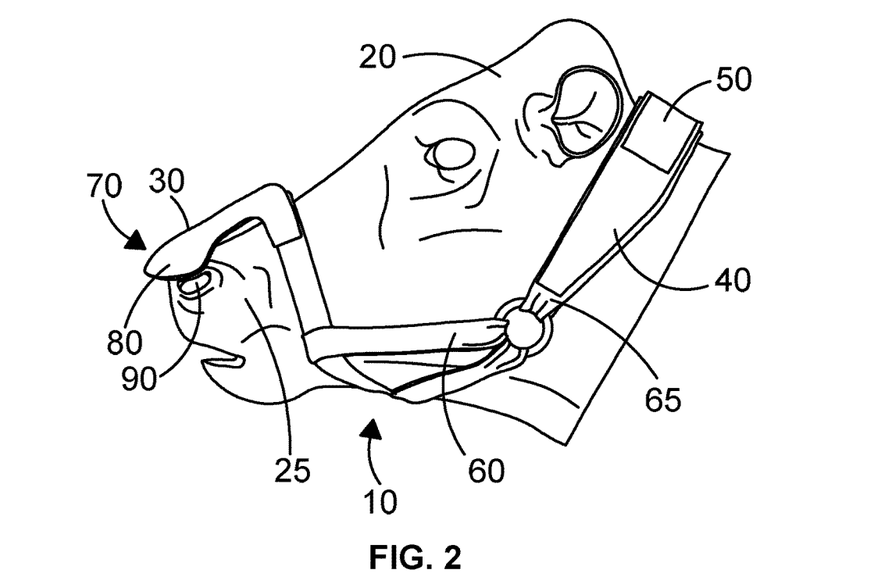
FIG. 2 depicts a side view of the animal emission monitoring device of FIG. 1 positioned on the head of a cow, in use.

With reference to FIGS. 1 and 2, there is illustrated an emission monitoring device 10, in use, mounted on the head of a cow 20. The emission monitoring device 10 comprises a snout member 30 positioned on the snout 25 of the cow 20, such that the snout member 30 extends from the upper side of the head of the cow 20. The device 10 further comprises a power means 40 and positioning straps 60, the positioning straps 60 for positioning and retaining the device 10 on the head of the cow 20. The snout member 30 comprises a sensor unit 70 which projects over the nostrils 90 of the cow 20.

In this embodiment, the snout member 30 is made from a semi-flexible rubber casing and sits on the upperside of the snout 25 of the cow 20. The longitudinal axis of the snout member 30 is parallel to the longitudinal axis of the snout 25. The snout member 30 is symmetrical along its longitudinal axis and sits on the snout 25 such that it extends symmetrically over the snout 25.

The snout member 30 is substantially Y-shaped, such that the main body of the snout member 30 extends the length of the snout 25 and the upper portion of the Y shape of the snout member 30 extends beyond the width of the snout 25, over the nostrils 90 of the cow. In this embodiment, the main body of the snout member 30 extends across the width of the top of the snout 25 and is slightly curved about its longitudinal axis, such that the snout member 30 follows the curve of the snout 25.

In other embodiments, it is envisaged that the main body of the snout member 30 is substantially flat in the horizontal plane and does not extend across the width of the snout 25. Alternatively, the snout member 30 is wider than the width of the snout 25 and consequently curves around the snout 25 such that the snout member 30 remains proximate the surface of the snout 25. In this way, the snout member 30 is non-intrusive and does not interfere with the cow's 20 vision, feed or water intake, rumination or other normal behaviour.

The greatest point of methane emission from cattle is the nostril. As such, the device 10 extends from the upper side of the head of the cow 20 such that a portion of the snout member 30 is positioned proximate the nostrils of the cow 20.

The snout member 30 comprises a sensor unit 70. The sensor unit 70 is proximate the end of the snout member 30 removed from the head of the cow 20. The portion of the snout member 30 containing the sensor unit 70 projects over the nostrils 90 of the cow 20.

The sensor unit 70 comprises two methane sensors 80, 85. Each sensor 80, 85 collects methane emission data. The two sensors 80, 85 are set apart on the snout member 30 symmetrically about the longitudinal axis of the snout member 30, labelled A-A on FIG. 1. In this way, each sensor 80, 85 is proximate each nostril 90 of the cow 20. Each sensor 80, 85 detects the quantity of gas emissions present at the location of the sensor 80, 85 at a point in time.

The sensors 80, 85 take continuous measurements of the methane present. The data may be taken at a rate of 20-100 ms. In this way, an accurate map of emissions is taken from the cow 20. Alternatively, it is envisaged that the sensors 80, 85 monitor methane intermittently. In this way, a smaller quantity of data is collected over a time period and reduced data processing power is required. As such, the sensors 80, 85 may collect data at a slower rate, or data may be collected continuously for a period of time followed by a period of no data collection. This allows emission monitoring only during certain periods of interest such as at night or during feeding periods. As such, in embodiments of the present claimed invention, the user may control or programme the data collection rate of the sensors 80, 85.

Figure 3:
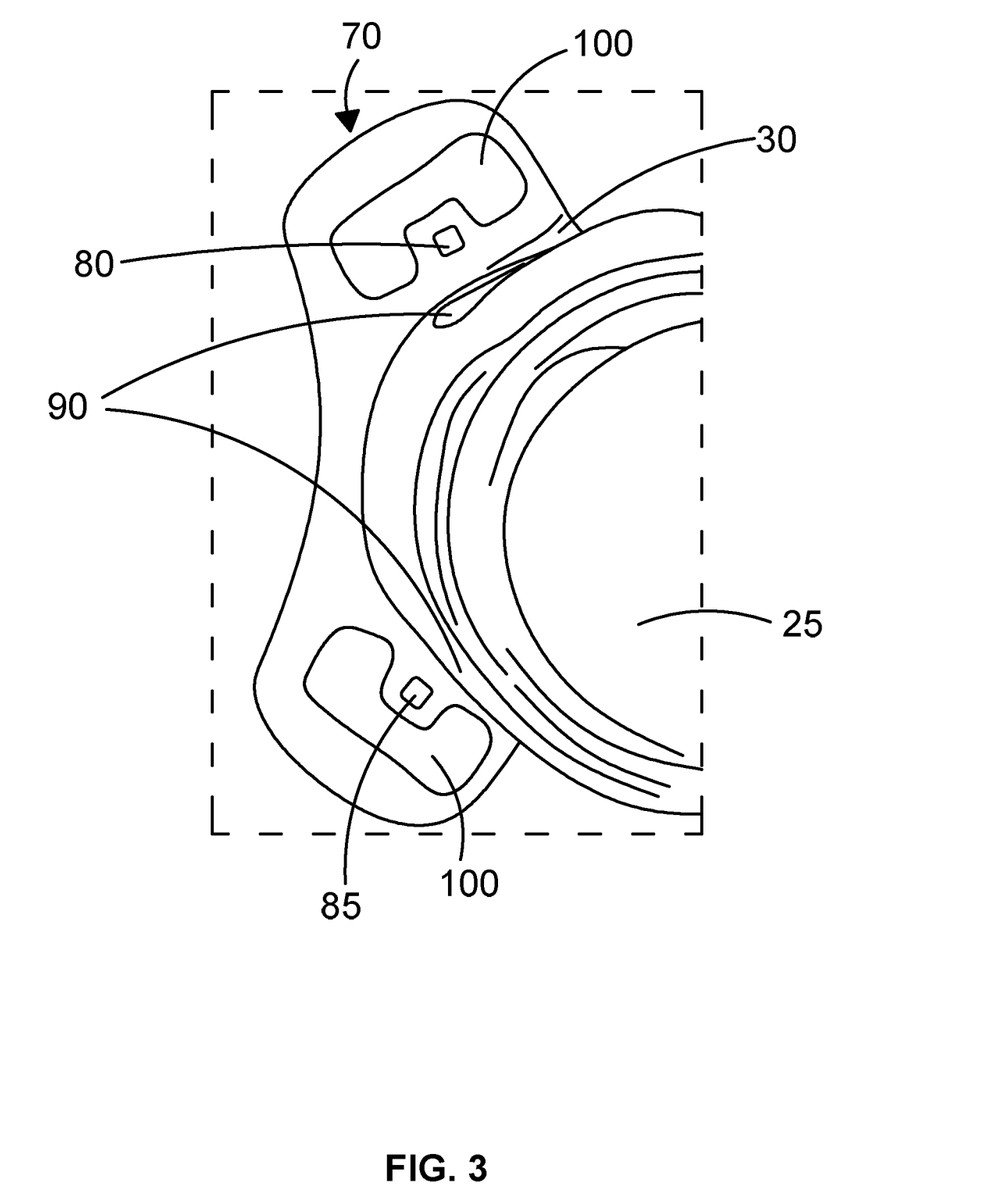
FIG. 3 depicts an underside view of a portion of the animal emission monitoring device of FIG. 1 positioned on the head of a cow, in use.

Each methane sensor 80, 85 is located on the underside of the snout member 30. FIG. 3 shows an embodiment of the present invention in use, wherein the underside of the snout member 30 is shown. The sensors 80, 85 are positioned 2 cm away from each nostril 90.

The sensors 80, 85 are fast response sensors. Each sensor 80, 85 comprises a means for waterproofing, such as a filter. In this way, the sensor 80, 85 is reasonably protected from moisture and fluid damage.

In other embodiments, the sensor unit 70 may contain only one methane sensor 80, 85 positioned in a similar fashion over one of the nostrils 90 of the cow 20, or a plurality of methane sensors 80, 85. Data from a single nostril 90 can consequently be used to model gas emission from the entire cow 20.

Furthermore, in other embodiments it is envisaged that the sensor unit 70 comprises a carbon dioxide sensor. Alternatively, the sensor unit 70 comprises two carbon dioxide sensors, each proximate the two nostrils 90 of the cow 20. As such, it is envisaged that the device 10 may comprise four sensors 80, 85 such that a methane sensor 80, 85 and a carbon dioxide sensor are located proximate each other and proximate each nostril 90 of the cow 20.

The sensor unit 70 further comprises a microprocessor 100. The microprocessor is suitable encased within the snout member 30 or protected on the sensor unit 70 from moisture and other damage. The microprocessor 100 is fitted with Bluetooth or W-Fi connectivity means. In this way, data from the sensors 80, 85 can be transmitted wirelessly to a gateway, user device or other suitable receiving and data storage means. As such, the user may access the data from the sensor unit 70 through a mobile app or web dashboard.

The data from the sensor unit 70 may be transmitted wirelessly in real time. In this way, live data is received by the user, for example, through the gateway as it is collected. This data may then be viewed or processed further. This data may then be used to inform on efficiency metrics, behaviour, health and other emission-related statistics.

In the case that the cow 20 and the sensors 80, 85 are too far away from the gateway, user device or other suitable receiving means such that the data cannot be received, the data may temporarily be stored locally on each device 10. In this way, the data is temporarily stored until proximity to the receiving means is such that the data can be transferred and/or offloaded.

Alternatively or additionally, the data collected from the sensor unit 70 may be permanently stored in a storing means located on the device 10. The storing means may comprise an SD card or other suitable local data storing means. In this way, a 'hard' copy of the data is stored. The storing means may then be accessed and removed by the user and consequently cleared of data and returned to the device 10.

Post processing of the data from the sensor unit 70 may be undertaken such as conversion of the analogue data to gas concentration in parts per million (ppm). This data may be displayed in a readable form, such as graphics. This data may provide the user with insight into the wellbeing, digestive performance, indication of disease and/or estrous state of the animal. Additionally, this data may be used to compare the gas emissions of individual cattle, herds or regions.

In this embodiment, the microprocessors 100 are powered by a power means 40, such as a lithium polymer or lithium ion battery. The device 10 is designed to be positioned on the head of the cow 20 for an extended period of time, such as a number of weeks or months. As such, this power means 40 requires recharging. A solar cell 50 is used to harness solar energy from the natural external environment of the cow. The solar cell 50 then automatically converts the solar energy in to electrical energy with which to recharge the power means 40, without the need for user interaction. Alternatively, it is envisaged that the user manually recharges the power means 40.

The snout member 30 is attached to the positioning straps 60 at the end of the snout member 30 removed from the nostrils 90. As such, the snout member 30 is suitably rigid such that it sits unsupported along the length of the snout 25. Alternatively, the snout member 30 is in partial or full contact with the snout 25.

The positioning straps 60 wrap from the snout member 30 in a continuous loop around the base of the snout 25, in such a way that motion of the cow's 20 jaw and mouth is not inhibited. In this embodiment, the positioning straps 60 further comprise a collar portion 65 which sits on the neck of the cow 20. The positioning straps 60 extend along the underside of the head and around the jaw of the cow 20 such that the positioning straps 60 meet at the collar portion 65.

The collar portion 65 is in contact with the neck of the cow 20 and extends symmetrically about the longitudinal axis of the neck of the cow 20. The collar portion 65 extends around a significant portion of the neck of the cow 20 and reduces the motion of the device 10 relative to the cow 20, during use. The positioning straps 60 and collar portion 65 are connected such that the device 10 extends, uninterrupted, around the head of the cow 20. In this way, the collar portion 65 aids with the retention of the device 10 on the head of the cow 20.

In this embodiment, the collar portion 65 also comprises the power means 40 and the solar cell 50. The solar cell 50 is rectangular and extends along the collar portion 65. The solar cell 50 sits in the centre of the collar portion 65, such that it is on the vertically highest point of the neck when the cow 20 is stood upright. In this way, the solar cell 50 is exposed to greatest solar energy from the sun during the cow's 20 daily activities.

The power means 40 is proximate the solar cell, and is recharged by the solar cell 50. The solar cell 50 requires 2 full hours of sunlight to fully re-charge the power means 40. In this way, the power means 40 may operate for 15 days before recharging is required. Alternative recharging and operating times are envisaged.

Means to connect the solar cell 50, power means 40 and sensors 80, 85 are provided such as wiring passing through the positioning straps 60 from the collar portion 65 to the snout member 30.

The positioning straps 60 and collar portion 65 may be formed from a single member or may comprise a plurality of members connected together. The collar portion 65 may be connected to the positioning straps 60 using any suitable connecting means. It is envisaged that the positioning straps 60 and/or collar portion 65 are adjustable such that the device 10 may be fitted to cattle of various shapes and sizes of snouts 25 and heads.

Alternative configurations of the positioning straps 60 are envisaged. For example, the positioning straps 60 may extend along any regions of the head and neck of the cow 20 including, but not limited to, over the crown of the head, under the ears or along the jaw of the cow 20. The collar portion 65 may sit on an alternative portion of the head of the cow 20 or alternatively the device 10 may not comprise a collar portion 65. Alternatively, the positioning straps 60 may not extend beyond the snout 25 of the cow 20 such that the device 10 is positioned entirely on the snout 25. Positioning of the device 10 on the cow 20 considers the need for the device 10 to not inhibit the cow's 20 normal behaviour.

The purpose of the positioning straps 60 is to position the device 10 on the head of the cow 20, and further to retain the device 10 in this position during use. In this embodiment, the device 10 is removably retained on the head of the cow 20 such that the device 10 may be removed, for example, for user access, animal health and welfare checks, maintenance or at end of use of the device 10.

The device 10 is suitable for long-term use on the cow 10. As such, the device 10 is lightweight, non-intrusive and positioned on the head of the cow 20 such that normal behaviour of the cow 20 is not disrupted. The collar portion 65 may be suitably cushioned and the positioning straps 60 be formed from a suitable material such that the device 10 does not cause the cow 20 discomfort. Lack of comfort of the device 10 may consequently lead the cow 20 to try to remove the device 10. This is not desired as damage to the device 10 or dislodging from the preferred position of the device 10 may occur.

Figure 4:
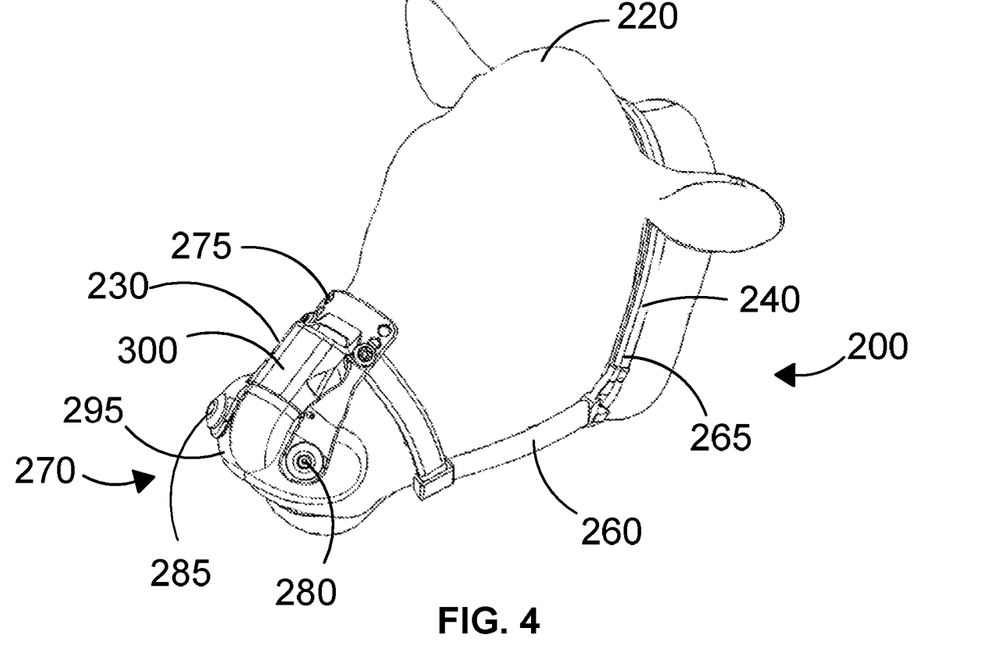
FIG. 4 depicts a perspective view of a second embodiment of the animal emission monitoring device in accordance with the present claimed invention positioned on the head of a cow, in use.
Figure 5:
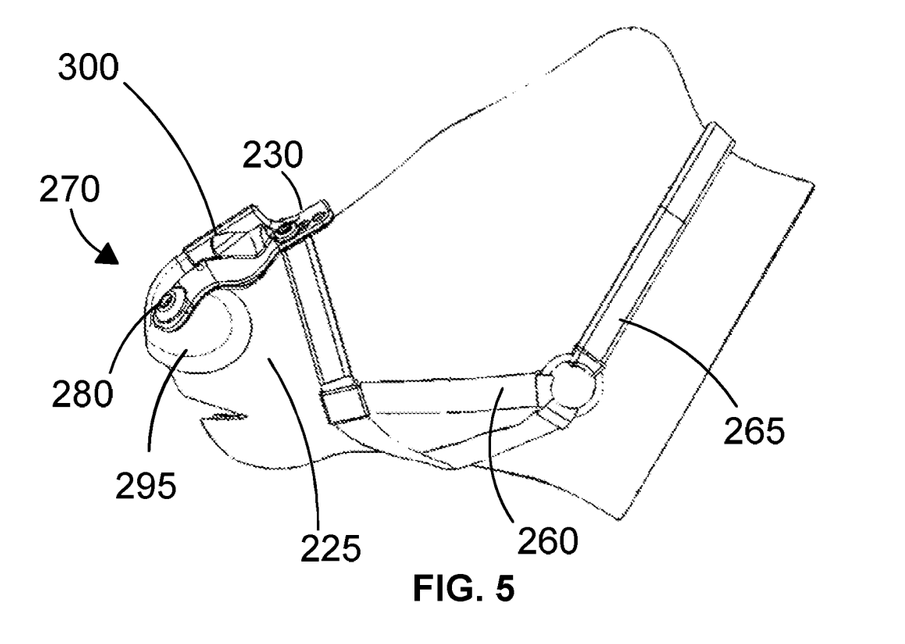
FIG. 5 depicts a side view of the animal emission monitoring device of FIG. 4 positioned on the head of a cow, in use.

With reference to FIGS. 4 and 5, there is illustrated a second embodiment of an emission monitoring device 200 in accordance with the first aspect of the invention, in use, mounted on the head of a cow 220. The emission monitoring device 200 comprises a snout member 230 positioned on the snout 225 of the cow 220, a sensor unit 270 comprising methane sensors 280 and 285, power means 240, positioning straps 260 and a collar portion 265 similar to those of the first embodiment outlined in FIG. 1.

The emission monitoring device 200 additionally comprises a flexible member 295. The flexible member 295 comprises resiliently deformable rubber and is attached to the snout member 230 via first attachment means 205 such that the flexible member 295 is located over the nostrils of the cow 220, in use. The flexible member 295 and snout member 230 assembly is substantially T-shaped.

The flexible member 295 is curved such that the flexible member 295 extends over and beyond both nostrils of the cow 220. The flexible member 295 extends the width of the snout 225, shielding the cow's 200 nostrils from the external environment. In this way, the interference of wind, contaminants, and pre-dispersion of the exhalation on the measurements taken by the sensors of the device 200 is reduced. The flexible member 295 is configured such that the flexible member 295 does not inhibit function of the sensor unit 270 and instead aids accurate methane capture.

The profile of the snout member 230 and flexible member 295 is relatively flat against the snout 225 such that the emission monitoring device 200 is non-intrusive and does not interfere with the cow's 220 vision, feed or water intake, rumination or other normal behaviour. Additionally, the flexible member 295 is detachable from the snout member 230 via the first attachment means 205 such that the size of the flexible member 295 can be selected as appropriate for the size and snout characteristics of the cow 220.

The snout member 230 comprises the sensor unit 270. The sensor unit 270 comprises a temperature sensor, an inertial sensor and a location tracker. The additional data provided by each sensor allows the emission conditions to be monitored alongside data capture from the methane sensor. The snout member 230 further comprises an elongate channel 300 located along the longitudinal axis, labelled A'-A' on FIG. 4, of the snout member 230. The methane sensor and a differential pressure sensor 305 are located within the channel 300 such that the methane sensor and the differential pressure sensor 305 are adjacent.

A filter is located at a first end of the channel 300a for preventing feed, mud, grass and other contaminants from entering the channel 300 and interfering with sensor function. It is envisaged that the filter may be any suitable filter or plurality of filters such as a mesh filter, PTFE (polytetrafluoroethylene) filter or a pleated PTFE filter.

The snout member 230 is attached to the positioning straps 260 at the end of the snout member 230 removed from the nostrils of the cow 220. The snout member 230 is adjustable such that the length that the snout member 230 extends along the snout 225 can be altered. In this embodiment, the snout member 230 is adjustable between three discrete positions by second attachment means 275. In FIGS. 4 and 5 the snout member 230 is positioned to provide the shortest reach over the snout 225.

Figure 6:
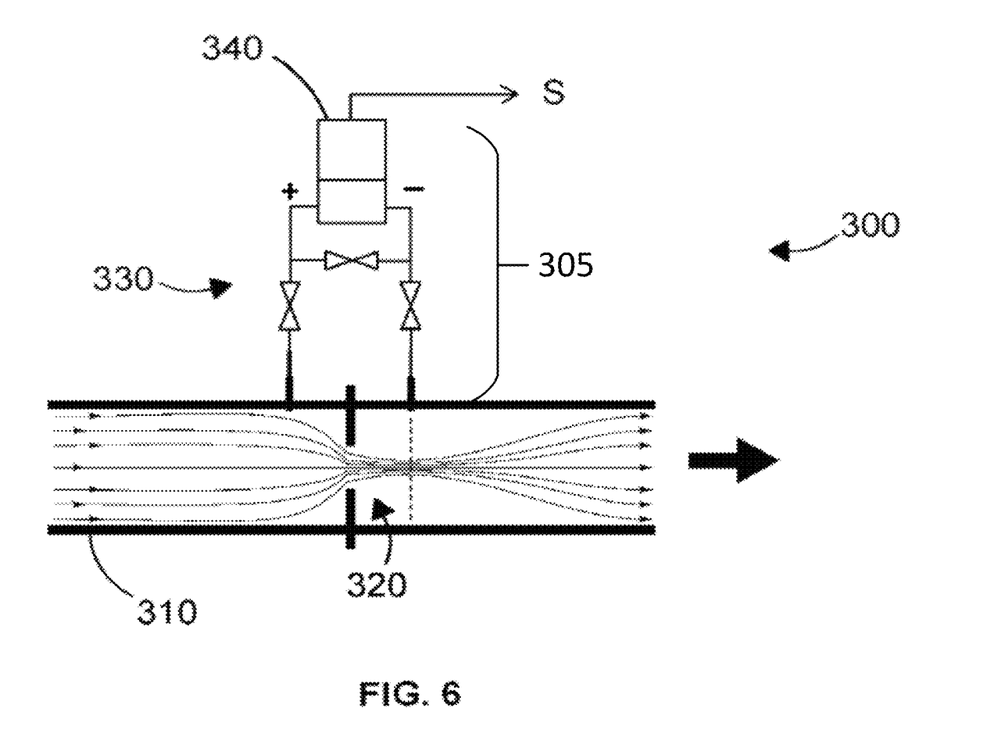
FIG. 6 depicts the differential pressure sensor of the animal emission monitoring device of the second embodiment.

FIG. 6 depicts the differential pressure sensor 305 of the emission monitoring device 200 of the second embodiment. The methane concentration measurement of the methane sensor and the measurements of the differential pressure sensor 305 can be used to determine the quantity of methane produced by the cow 220 over a time period. Corresponding methane purities with the total quantity of gas exhaled by the cow 220 allows the amount of methane exhaled by the cow 220 to be determined, and, as such, the differential pressure sensor 305 is advantageous in quantifying the cow's methane emissions.

To measure the volumetric flow rate, the differential pressure sensor 305 measures the change in static pressure on either side of an orifice 320 located within a pipe 310 using a three valve manifold 330 and a differential pressure transducer 340. The Venturi effect is observed when the fluid within the pipe 310 passes through the orifice 320 and, in use, the pressure differential between both sides of the orifice 320 is measured. The differential pressure transducer 340 outputs a signal S and this data can be monitored and processed.

The arrangement of the differential pressure sensor 305 and the flexible member 295 allow a substantial portion of the exhaled emissions of the cow's 220 nostrils to pass through the channel 300 and the differential pressure sensor 305. The shielding nature of the flexible member 295 and snout member 230 assists in preventing pre-dispersion of the exhalation prior to sensor capture of the methane sensor and the differential pressure sensor 305.

Further embodiments within the scope of the present invention may be envisaged that have not been described above, for example, there may be different types and combinations of sensors located on the sensor unit 70 or on other portions of the device 10. Other means of sending and receiving data from the sensor unit 70 is envisaged, as well as alternative methods for the user to access the data. The materials of the device 10 must be suitable for outdoor exposure and other material combinations may be envisaged. Additionally, the device 10 may be used on other bovine animals, or a range of other animals such as sheep and goats. It is envisaged that embodiments of the present claimed invention may, in use, monitor the emissions of a range different gases from a range of animals. As such, the device 10 is not limited to use on cattle. The invention is not limited to the specific examples or structures illustrated, a greater number of components than are illustrated in the Figures could be used, for example.

The invention claimed is:

1. An animal emission monitoring device for positioning on a livestock animal, said animal emission monitoring device comprising:
   a snout member configured to be positioned on an upper side of a head of the livestock animal such that a longitudinal axis of the snout member is arranged substantially along the upper side of the head extending toward a snout of the livestock animal, the snout member being substantially Y-shaped, such that a main body of the snout member extends along a length of the head and an end portion of the snout member is forked into a Y shape to extend beyond a width of the snout and over nostrils of the livestock animal;
   a first sensor of the snout member configured to measure methane concentration in gas exhaled by the livestock animal, wherein the first sensor is disposed on an underside of a branch of the Y shape of the snout member;

a second sensor of the snout member configured to measure a quantity of gas exhaled by the livestock animal in a time period;

a microprocessor configured to transmit measurements taken by the first sensor and the second sensor to enable determination of an amount of methane exhaled by the livestock animal in the time period; and positioning means for positioning the device on the head of the livestock animal such that the snout member locates the first sensor proximate a nostril of the livestock animal.

2. The animal emission monitoring device according to claim 1, wherein at least said first sensor of said snout member is 1-2 cm from the nostril of the livestock animal, in use.

3. The animal emission monitoring device according to claim 1, further comprising a sensor unit, wherein said sensor unit is configured to collect data continuously.

4. The animal emission monitoring device according to claim 1, further comprising a sensor unit, wherein said sensor unit is configured to monitor intermittently.

5. The animal emission monitoring device according to claim 1, wherein said device further comprises a storing means for storing data collected from a sensor unit comprising the first sensor and the second sensor.

6. The animal emission monitoring device according to claim 1, wherein the microprocessor is configured to transmit data wirelessly to a gateway or user device.

7. The animal emission monitoring device according to claim 6, wherein said sensor unit is configured to transmit data in real time.

8. The animal emission monitoring device according to claim 1, wherein said device further comprises a power means.

9. The animal emission monitoring device according to claim 8, wherein said power means comprises a battery.

10. The animal emission monitoring device according to claim 9, wherein said power means comprises a solar cell.

11. The animal emission monitoring device according to claim 10, wherein said battery is configured to be recharged by said solar cell.

12. The animal emission monitoring device according to claim 1, further comprising a sensor unit, wherein said sensor unit comprises at least one carbon dioxide sensor.

13. The animal emission monitoring device according to claim 1, wherein said device is waterproof.

14. The animal emission monitoring device according to claim 1, further comprising a pipe of the snout member through which the gas exhaled by the livestock animal is passed and wherein the first sensor is configured to measure methane concentration of the gas exhaled by the livestock animal.

15. The animal emission monitoring device according to claim 1, wherein the second sensor comprises at least one pressure sensor.

16. The animal emission monitoring device according to claim 15, wherein the pressure sensor is a differential pressure sensor.

17. The animal emission monitoring device according to claim 1, wherein the second sensor comprises at least one flow rate sensor for measuring fluid flow rate.

18. The animal emission monitoring device according to claim 1, wherein the device comprises at least one temperature sensor.

19. The animal emission monitoring device according to claim 1, wherein the device comprises at least one inertia sensor.

20. The animal emission monitoring device according to claim 1, wherein the device comprises at least one location tracker.

21. The animal emission monitoring device according to claim 1, wherein the device comprises at least one filter.

22. The animal emission monitoring device according to claim 1, further comprising a sensor unit comprising the first sensor and the second sensor, wherein said sensor unit is configured to monitor at discrete intervals.

23. The animal emission monitoring device according to claim 1, further comprising an orifice located within a pipe of the snout member through which the gas exhaled by the livestock animal is passed, wherein the orifice is configured to allow the gas exhaled by the livestock animal to be passed through the orifice.

24. The animal emission monitoring device of claim 1, further comprising a flexible member that is configured to be detachably attached to the snout member and extend over and beyond nostrils of the livestock animal, wherein the flexible member is configured to protect at least the second sensor from external elements.

* * * * *